(12) United States Patent
Poucher et al.

(10) Patent No.: US 11,413,150 B2
(45) Date of Patent: Aug. 16, 2022

(54) INFLATABLE PENILE PROSTHETIC SYSTEM HAVING A TUBING ASSEMBLY INSERTABLE INTO A PENILE PROSTHESIS

(71) Applicant: Coloplast A/S, Humlebaek (DK)

(72) Inventors: Neal Poucher, North Oaks, MN (US); Mark A. Moschel, Plymouth, MN (US); Wei Zhang, Eden Prairie, MN (US)

(73) Assignee: Coloplast A/S, Humlebaek (DK)

( * ) Notice: Subject to any disclaimer, the term of this patent is extended or adjusted under 35 U.S.C. 154(b) by 237 days.

(21) Appl. No.: 16/912,082

(22) Filed: Jun. 25, 2020

(65) Prior Publication Data

US 2020/0345498 A1    Nov. 5, 2020

Related U.S. Application Data

(63) Continuation of application No. 15/885,836, filed on Feb. 1, 2018, now Pat. No. 10,729,546.

(60) Provisional application No. 62/453,514, filed on Feb. 2, 2017.

(51) Int. Cl.
*A61F 2/26*    (2006.01)
*A61F 2/48*    (2006.01)

(52) U.S. Cl.
CPC .............. *A61F 2/26* (2013.01); *A61F 2/484* (2021.08); *A61F 2250/0003* (2013.01); *A61F 2250/0097* (2013.01)

(58) Field of Classification Search
CPC ........................................................ A61F 2/26
See application file for complete search history.

(56) References Cited

U.S. PATENT DOCUMENTS

| | | | | |
|---|---|---|---|---|
| 5,062,417 A | * | 11/1991 | Cowen | A61F 2/26 600/40 |
| 6,808,490 B1 | * | 10/2004 | Ling | A61F 2/26 600/40 |
| 8,147,400 B1 | * | 4/2012 | Daniel | A61F 2/26 600/40 |
| 2004/0225182 A1 | * | 11/2004 | Eid | A61F 2/26 600/38 |
| 2005/0014993 A1 | * | 1/2005 | Mische | A61F 2/26 600/40 |

* cited by examiner

*Primary Examiner* — John P Lacyk
(74) *Attorney, Agent, or Firm* — Coloplast Corp., Coloplast A/S; Nick Baumann

(57) ABSTRACT

An inflatable penile prosthetic system includes a tubing assembly insertable to a penile prosthesis and a pump adapted move liquid out of a reservoir and into the penile prosthesis.

10 Claims, 14 Drawing Sheets

INFLATABLE PENILE PROSTHETIC SYSTEM HAVING A TUBING ASSEMBLY INSERTABLE INTO A PENILE PROSTHESIS

BACKGROUND

Implanted penile prostheses have offered men suffering from erectile dysfunction with an erection that is suitable for penetrative intercourse. While the implantation procedure for a penile prosthesis has become highly refined over the course of years, there is the possibility of improving the patient comfort and for further refining the procedure.

In one approach to the implantation of the penile prostheses, each corpora cavernosum is dilated (opened) with an appropriate dilation tool to form a recess that is sized to receive one prosthesis of the two cylinders of the penile prostheses. Thereafter, a tool (referred to by surgical practitioners as a "Furlow" introducer) is inserted into each dilated corpora cavernosum to measure a length of the penis distally and proximally to determine a desired length of the cylinders to be implanted. A cylinder of the appropriately selected length is secured to a suture, and the suture is secured to a needle (sometimes called a "Keith" needle). The Keith needle is attached to the Furlow introducer. The surgeon inserts the Furlow introducer into the dilated corpora cavernosum and pushes the Keith needle from of the introducer, through tissue of the penis, and out the glans penis. The exposed portion of the needle is handled by the surgeon, removed from the suture, and discarded. The remaining suture is subsequently employed to tow the cylinder into place inside of the dilated corpora cavernosum.

Patients and surgeons would welcome an alternative procedure that does not include puncturing of the glans penis.

SUMMARY

Aspects of the embodiments described in this patent application provide a system and a device and a method of implanting a penile prosthesis into a penis. Aspects of the embodiments described in this patent application provide a system and a device and a method of implantation of a penile prosthesis that obviates the use of a needle, and thus obviates the penetration of the glans penis by the needle, which allows for a more efficient implantation of the penile prosthesis with a quicker recovery time for the patient.

Embodiments provide a penile prosthetic that includes a helical feature on an exterior surface of the prosthetic, where the helical feature allows the prosthetic to be advanced into the corpora cavernosum with a twisting motion. In one embodiment, the helical feature is provided as a recess formed in an exterior surface of the prosthetic. In one embodiment, the helical feature is provided as a raised thread or engagement surface formed as a prominence on an exterior surface of the prosthetic. In one embodiment, the raised thread is absorbable by the body. Aspects include providing the penile prosthetic with a level of rigidity that allows the twisting motion to advance the prosthetic into the corpora cavernosum. In one embodiment, the rigidity is achieved through a disposable insert that is placed inside of the penile prosthetic and employed for the implantation step prior to disposal of the insert. In one embodiment, the rigidity is achieved by inflating the penile prosthetic with an amount of liquid that supports twisting of the penile prosthetic for advancement into the corpora cavernosum.

Embodiments provide a penile prosthetic that includes a primary lumen adapted to retain an amount of inflation liquid and a separate lumen provided with or containing a rigid spine or a rigid rod. The rigid spine or the rigid rod is suitably provided by a stiff polymeric material or a metal, such as stainless steel. The rigid spine, when inserted into the separate lumen, provides column strength to the penile prosthetic to allow the surgeon to push the penile prosthetic in a distal direction into the corpora cavernosum. In one embodiment, two or more separate lumens are provided with a rigid spine, where each rigid spine is separated by a radial distance from an adjacent rigid spine to provide the penile prosthetic with a sufficient column strength to allow the surgeon to insert the penile prosthetic into the corpora up to the glans. In one embodiment, the rigid spine that is retained within the lumen is removable after implantation of the penile prosthetic. The empty lumen may remain empty, or the empty lumen may be filled with a liquid. The volume of the primary lumen is at least a factor or 5, and preferably a factor of 20, and more preferably a factor of 40 or more times larger than any one of the separate lumen(s).

Embodiments provide a hollow base provided with a through channel sized to allow an insertion tool (or pushrod) to be inserted through the hollow base and into the penile prosthesis. The penile prosthesis includes a rounded distal end sized for implantation into the glans penis, an inflatable body connected to the rounded distal end, and a proximal base that terminates in a tip. The proximal base is adapted for insertion into the crus penis. In one embodiment, an elongated channel is formed axially through the proximal base to communicate with the inflatable body. A tool, suitably sized for insertion into the elongated channel, is employed to provide the penile prosthesis with a rigid delivery module that allows the surgeon to push the rounded distal end of the penile prosthesis into the glans penis. The tool is removed after the penile prosthesis is seated within the glans penis. The elongated channel is subsequently plugged with a cap or a plug that is adapted to prevent the inflation liquid inside of the inflatable body from leaking out of the penile prosthesis. In one embodiment, the plug resembles a rear tip extender or a cap that is sized to snap onto or couple with to provide the proximal base with a rounded proximal tip. In this embodiment, the tip extender or the cap has an outside diameter that is approximately equal in size to the outside diameter of the proximal base at the location where the tip extender is connected to the proximal base. The plug includes a central projection that is sized to fill and plug the elongated channel, a radial sleeve that is sized to surround and blend smoothly with an exterior surface of the proximal base, and a rounded proximal tip. In one embodiment, the tip extender or the cap has an outside diameter that is measurably smaller than the outside diameter of the proximal base at the location where the tip extender is connected to the proximal base. In one embodiment, the proximal base and the plug/cap are compatible with rear tip extenders that are attached to the proximal base to increase an overall length of the prosthesis. In one embodiment, the pushrod or insertion tool includes a length measuring indicia and is suitable for use as a measuring tool.

Embodiments provide a tool for insertion of a penile prosthetic into the corpora cavernosum. The tool includes a hinge that allows the tool to open and engage with a distal end a portion of the penile prosthetic. The tool, when engaged with the penile prosthetic, is inserted into the corpora cavernosum to deliver the distal end portion of the penile prosthetic into the glans penis. The penile prosthetic is released from the tool, and the tool is withdrawn from the corpora cavernosum.

Embodiments provide a tool for insertion of a penile prosthetic into the corpora cavernosum. The tool is provided as a rigid rod formed from a salt. The rod is inserted into the corpora cavernosum to provide the penile prosthetic with a column strength that allows the surgeon to deliver the distal end portion of the penile prosthetic into the glans penis. The salt rod is adapted to dissolve when the inflatable bladder of the penile prosthetic is filled with liquid. Embodiments provide dissolving the salt rod and extracting the resulting increased concentration of saline out of the inflatable bladder prior to subsequently inflating the inflatable bladder with a lower concentration of saline solution or water.

Embodiments provide a penile prosthetic having a distal tip that includes an injection site. The distal tip of the penile prosthetic is provided as a thin-walled balloon that is adapted to expand when inflated with liquid. The penile prosthetic is inserted into the corpora cavernosum with the distal tip near the glans penis. The surgeon injects a liquid into the injection site provided in the distal tip. The inflation of the distal tip allows the distal tip to more perfectly fill the glans penis, provide a more lifelike glans penis, reduces the likelihood of a floppy glans, and adds length to the penile prosthetic and to the penis after implantation.

Embodiments provide a penile prosthetic provided with a dual wall, needleless, two-piece design. A pair of bladders is bonded to the proximal base of the penile prosthetic. In one embodiment, a pair of inflatable bladders is bonded to the proximal base of the penile prosthetic. An elongated hole is formed in the proximal base and is sized to receive a flexible rod that is employed to insert the penile prosthetic into the corpora cavernosum. The dual wall design reduces the volume of liquid that is needed to inflate the inflatable bladder. In one embodiment, the second bladder is oriented in a side-by-side arrangement with the first bladder such that the pair of bladders is parallel and not coaxial. In one embodiment, the second bladder concentrically surrounds the first bladder such that the pair of bladders is coaxial. In one embodiment, a central bladder is provided that is concentrically surrounded by a second bladder, where the central bladder is adapted to receive an insertion tool for implantation of the penile prosthetic into the corpora cavernosa. In this embodiment, after removal of the insertion tool the central bladder may be filled with a material and sealed, leaving the second bladder as the sole inflatable bladder of the penile prosthetic. In this manner, less liquid is employed to achieve complete inflation of the penile prosthetic.

Embodiments provide a penile prosthetic having a distal tip, an inflatable body connected to the distal tip, a proximal tip connected to the inflatable body, and a removable tubing section. The removable tubing section is provided as a strain relief that is adapted for attachment to tubing that extends from a liquid reservoir. With the removable tubing section removed from the penile prosthetic, an opening is provided that allows insertion tool to be inserted inside of the inflatable body for insertion of the penile prosthetic into the corpora cavernosum. After implantation of the penile prosthetic, the tool is removed and the strain relief (or removable tubing section) is connected to the penile prosthetic and the additional length of reservoir tubing is connected to the removable tubing section.

Embodiments provide an inflatable penile prosthetic system including a pump adapted for attachment to a reservoir; a penile prosthetic assembly including: an inflatable bladder having a distal end sized for placement within a glans penis, a base connected to the inflatable bladder, with base including an interior channel extending an entire length of the base from a hole formed in a proximal end of the base to the inflatable bladder, and a tubing port coupled to an exterior surface of the base, with the tubing port adapted for attachment to the pump, a plug sized for insertion into the hole; and a push rod. The pushrod has a diameter that is sized for insertion into the hole, with the push rod having a length that is adapted to extend from the distal end of the inflatable bladder, through the interior channel of the base, and out of the hole formed in the base. Advantages provided by the system include a prosthetic that is implantable deep inside of the corpora cavernosum without the aid of a Keith needle. The pushrod pushes the prosthetic the full length of the corpora cavernosum. After removal of the pushrod, the plug is inserted into the hole to provide a pressurized seal for the prosthetic.

Embodiments of the inflatable penile prosthetic system include where the plug has at least one barb. The advantages of the barb ensure that the barb is easy to insert into the channel in the base and very difficult to remove, thus the plug provides a lasting pressurized seal for the implant. The number of barbs on the plug may vary. The radial extent of the barbs relative to the stem of the plug may vary to provide a range of sealing engagement between the barbs and the channel in the base. The depth of engagement of the barbs inside of the channel in the base may vary, as can the number of barbs distributed along the stem of the plug.

Embodiments of the inflatable penile prosthetic system include where the plug has a first barb and a second barb, where the first barb and the second barb are configured to engage with the interior channel of the base to provide a pressurized seal for the penile prosthetic assembly. Advantages of the plurality of the barbs work to ensure that the plug is very difficult to remove, thus the plug provides a lasting pressurized seal for the implant.

Embodiments of the inflatable penile prosthetic system include where the plug is a single integrated piece formed from a single polymer. Advantages of this feature include simplicity of fabrication and ensure that plug having a proper hardness to be inserted into the hole of the prosthetic easily by a surgeon wearing gloves.

Embodiments of the inflatable penile prosthetic system include where the plug has a barb section and a proximal end section, with the barb section formed of a first polymer having a first durometer and the proximal section is formed of a second polymer having a second durometer, where the second durometer is of a lower value than the first durometer. Advantages of this embodiment are that the plug has barbs that are harder than the plug proximal end, so the proximal end is soft/comfortable to the patient and the barbs are durable and configured to engage with the hole in the prosthetic.

Embodiments of the inflatable penile prosthetic system include where the pushrod includes uniform markings that allow the pushrod to be used as a ruler. Advantages of this embodiment obviate the use of a Furlow tool. Since the system obviates the use of a needle, the system also obviates the use of a Furlow tool, which is commonly provided as a separate tool during an implantation procedure. Thus, the system and the kit of parts can be provided as one set with no outside parts to be tracked and maintained.

Embodiments of the inflatable penile prosthetic system include where the penile prosthetic assembly includes an artificial glans penis provided on a distal end portion of the inflatable bladder, with a width of the artificial glans penis wider than a width of the inflatable bladder. Advantages of this embodiment provide an implant that offers the user greater girth and a more natural feel at the distal end of the implant.

Embodiments provide a kit of parts having a pump adapted for attachment to a reservoir; a penile prosthetic assembly including an inflatable bladder having a distal end sized for placement within a glans penis, a base connected to the inflatable bladder, with base including an interior channel extending an entire length of the base from a hole formed in a proximal end of the base to the inflatable bladder, and a tubing port coupled to an exterior surface of the base, with the tubing port adapted for attachment to the pump, a plug sized for insertion into the hole; a push rod having a diameter that is sized for insertion into the hole; and a plurality of connectors including a first connector provided to attach first pump tubing to reservoir tubing and a second connector provided to attach second pump tubing to tubing of the penile prosthetic assembly. Advantages of the kit include a single package delivered to the surgical suite having all the components needed to implant a penile prosthetic. Other advantages of the kit include a system that obviates the use of a needle for placing the prosthetic in the corpora cavernosum.

Embodiment of the kit of parts provide the push rod with a length that is adapted to extend from the distal end of the inflatable bladder, through the interior channel of the base, and out of the hole formed in the base. Advantages of a long pushrod allow the surgeon to place the prosthetic in the dilated corpora cavernosum without pushing a needle through the glans penis. Typically, a needle is pushed through the glans penis, and a suture attached to the needle is used to tow the prosthetic into the corpora. The kit of parts obviates the use of such a needle.

Embodiment of the kit of parts provide a plug that is sized to engage with the interior channel of the base to provide a pressurized seal for the penile prosthetic assembly. Advantages of the plug provide for a leak-proof prosthetic. The number of barbs and the radial extent of the barbs relative to the stem of the plug may vary to provide a range of sealing engagement between the barbs and the channel in the base. The depth of engagement of the barbs inside of the channel in the base may vary.

Embodiment of the kit of parts provide the plug with a first barb and a second barb, where the first barb and the second barb are configured to engage with the interior channel of the base to provide a pressurized seal for the penile prosthetic assembly. Advantages of the barbs ensure that the plug remains engaged with the base of the prosthetic.

Embodiment of the kit of parts provide the pushrod with uniform markings that allow the pushrod to be used as a ruler. The pushrod advantageously can be used to measure both the proximal and distal dilated lengths of the penis.

Embodiment of the kit of parts provide the penile prosthetic assembly with an artificial glans penis provided on a distal end portion of the inflatable bladder, with a width of the artificial glans penis wider than a width of the inflatable bladder. Advantages of a wider glans area provides the glans of the penis with a full and more natural width.

Embodiments provide an inflatable penile prosthetic and a delivery device useful in placement of the inflatable penile prosthetic, comprising: a rounded distal end sized for implantation into the glans penis, an inflatable body connected to the rounded distal end, and a proximal base connected to the inflatable body, where the proximal base terminates in a tip and has an elongated channel formed axially through the proximal base to communicate with the inflatable body; a tool sized for insertion into the elongated channel, where the tool provides the penile prosthetic with a rigid delivery module that allows placement of the rounded distal end of the penile prosthetic into the glans penis; and a plug that is insertable into the elongated channel and adapted to prevent inflation liquid inside of the inflatable body from leaking out of the penile prosthetic. The plug has an outside diameter that is approximately equal in size to the outside diameter of the proximal base at the location where the plug is connected to the proximal base.

Embodiments of the inflatable penile prosthetic and a delivery device useful in placement of the inflatable penile prosthetic include a hollow proximal base.

Embodiments of the inflatable penile prosthetic and a delivery device useful in placement of the inflatable penile prosthetic include providing the plug as a rear tip extender that is sized to snap onto or couple with the proximal base to provide the proximal base with a rounded proximal tip.

Embodiments of the inflatable penile prosthetic and a delivery device useful in placement of the inflatable penile prosthetic include the plug having a central projection that is sized to fill and plug the elongated channel, a radial sleeve that is sized to surround and blend smoothly with an exterior surface of the proximal base, and a rounded proximal tip.

Embodiments of the inflatable penile prosthetic and a delivery device useful in placement of the inflatable penile prosthetic include the pushrod or insertion tool having a length measuring indicia and is suitable for use as a measuring tool.

Embodiments provide an inflatable penile prosthetic system including a pump adapted for attachment to a reservoir; a penile prosthetic assembly including: an inflatable bladder having a distal end sized for placement within a glans penis, a base connected to the inflatable bladder, with base including an interior channel extending an entire length of the base from a hole formed in a proximal end of the base to the inflatable bladder, and a tubing port coupled to an exterior surface of the base, with the tubing port adapted for attachment to the pump, a plug sized for insertion into the hole; and insertion aid that is an inflatable balloon that is intraoperatively insertable into the inflatable bladder of the penile prosthetic and removable from the inflatable bladder of the penile prosthetic.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
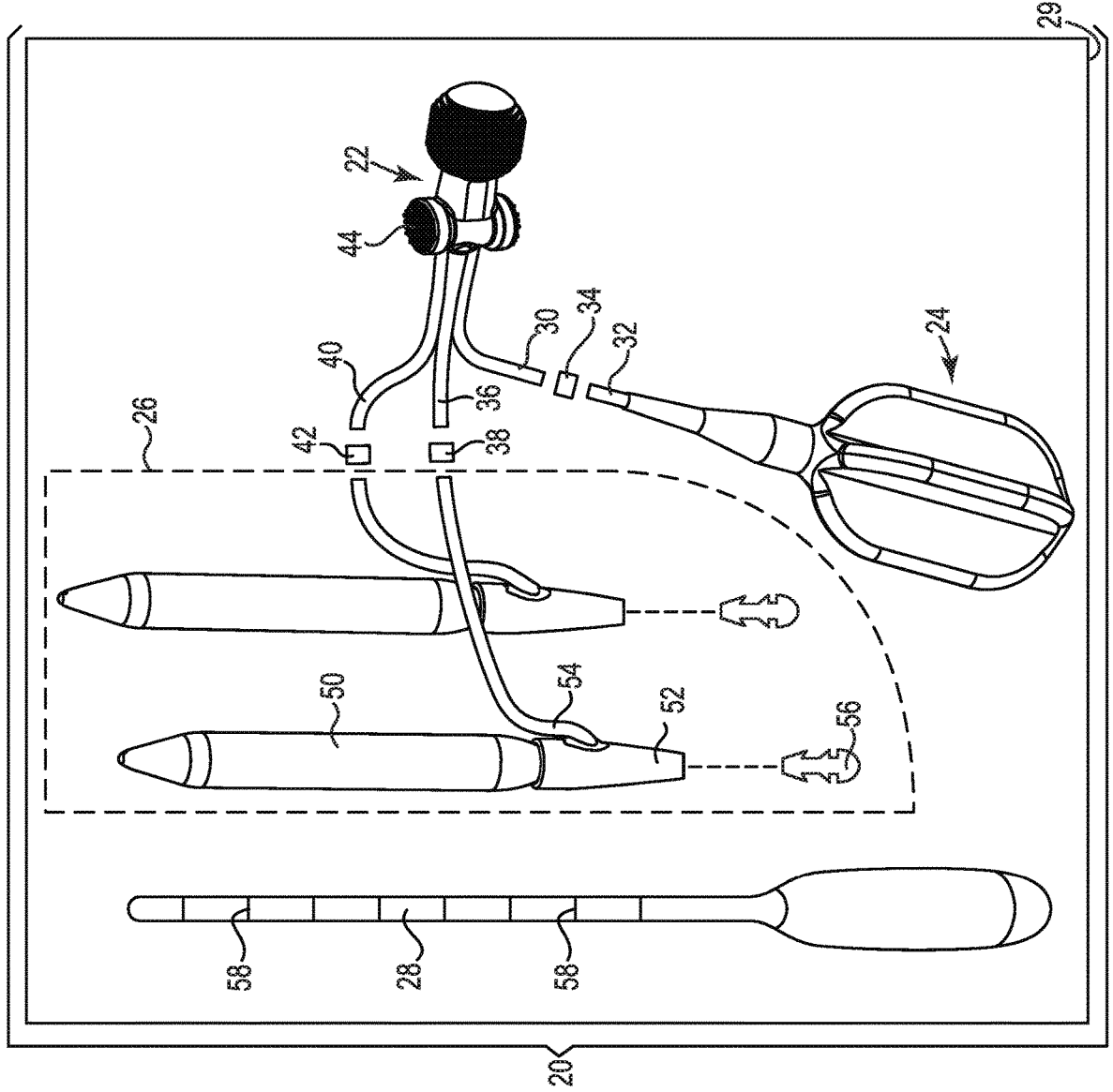
FIG. 1 is a perspective view of one embodiment of an inflatable penile prosthetic system including a pump attachable to a reservoir and a penile prosthetic assembly.

In the following detailed description, reference is made to the accompanying drawings. The drawings form a part of this specification and illustrate exemplary embodiments for practicing the invention. Directional terminology, such as "top," "bottom," "front," "back," "leading," "trailing," etc., is used with reference to the orientation of the Figure(s) being described. Because components of embodiments can be positioned in a number of orientations, the directional terminology is used for purposes of illustration and is in no way limiting. It is to be understood that other embodiments may be utilized and structural or logical changes may be made without departing from the scope of the invention. The detailed description describes examples for practicing the invention and is not to be read to limit the scope of the invention. The scope of the invention is defined by the attached claims.

End means endmost. Relative to an observer, for example a surgeon, a distal end is the furthest endmost location of a distal portion of a thing being described, whereas a proximal end is the nearest endmost location of a proximal portion of the thing being described. The portion next to or adjacent to an end is an end portion.

An implanted penile prosthetic has proven useful in treating erectile dysfunction in men. One acceptable implanted penile prosthetic includes two inflatable cylinders implanted in the penis, a pump implanted in the scrotum or other internal space of the body, and a liquid holding reservoir implanted in the abdomen or other internal space of the body, with the pump connected to the cylinders and the reservoir.

In an implantation procedure, the penis of the patient is incised in a corporotomy to expose a pair of corpora cavernosa that are aligned axially in a side-by-side orientation within the penis. A cutting implement, such as a curved Mayo scissors, is employed to penetrate the fascia of the penis and form an opening accessing each corpora cavernosum. Subsequently, each corpora cavernosum is dilated (opened) with an appropriate dilation tool to form a recess that is sized to receive one of the two cylinders of the penile prosthetic.

Thereafter, a tool (referred to by surgical practitioners as a "Furlow" introducer) is inserted into each dilated corpora cavernosum to measure a length of the penis distally and proximally to determine a desired length of the cylinders to be implanted. A cylinder of the appropriately selected length is secured to a suture, and the suture is secured to a needle (sometimes called a "Keith" needle). The Keith needle is attached to the Furlow introducer. The Keith needle could possibly fall out of the Furlow introducer, so the surgical staff handles the tool with care. The surgeon inserts the Furlow introducer into the dilated corpora cavernosum. The surgeon steadies the Furlow introducer with one hand and pushes a plunger (or obturator) of the Furlow introducer with the other hand. Pushing the plunger pushes the needle from of the introducer, through tissue of the penis, and out the glans penis. The exposed portion of the needle is handled by the surgeon, removed from the suture, and discarded. The remaining suture is subsequently employed to tow the cylinder into place within the dilated corpora cavernosum.

The above-described procedure has proven effective when implanting penile prostheses. However, surgeons would appreciate having fewer parts to handle during the procedure. In addition, surgeons and those handling the Keith needle would possibly welcome an approach for implanting a penile prosthetic that reduces or eliminates their exposure to the Keith needle.

Embodiments provide a system and a device and a method of implanting a penile prosthetic into a penis that obviates the use of the Keith needle, and thus obviates the penetration of the glans penis by the needle, which allows for a more efficient implantation of the penile prosthetic with a quicker recovery time for the patient.

FIG. 1 is a perspective view of one embodiment of an inflatable penile prosthetic system 20. The system 20 includes a pump 22 attachable to a reservoir 24 and a penile prosthetic assembly 26, and a pushrod 28 provided to aid in placing the penile prosthetic into penile tissue.

In one embodiment, the system 20 is enclosed in a package 29 that allows the system 20 to be provided to a healthcare facility as a kit of parts. The kit of parts 29 advantageously provides the healthcare facility with the implant and a delivery tool for placement of the implant.

The pump 22 includes a tube 30 that is attachable to a first tube 32 of the reservoir 24 by a first connector 34, a second tube 36 that is attachable to the penile prosthetic assembly 26 by a second connector 38, and a third tube 40 that is attachable to the penile prosthetic assembly 26 by a third connector 42. The connectors 34, 38, 42 are locking connectors that are designed to not separate from the tubing after attachment. The connectors 34, 38, 42 are employed to couple the reservoir 24 and the pump 22 after the penile prosthetic assembly 26 has been implanted.

The pump 22 operates to draw a liquid from the reservoir 24 and push the liquid into the penile prosthetic assembly 26 to inflate the prosthetic. The pump 22 also includes an activation surface 44 that, when activated, allows the liquid to flow out of the inflated prosthetic back into the reservoir 24. The activation surface 44 acts as a deflation button for the prosthetic.

The penile prosthetic assembly 26 includes two penile implants, where each of the penile implants is implantable into a dilated corpora cavernosum of the penis. Each of the penile implants is identical, and thus only one of the penile implants is described here for brevity.

Each of the penile implants of the penile prosthetic assembly 26 includes an inflatable bladder 50 connected to a base 52, a tubing port 54 connected to the base 52, and a plug 56 that is insertable into a proximal end of the base 52. The tubing port 54 includes a section of tubing that is attachable to the tubing 36 of the pump 22 by the connector 38.

The inflatable bladder 50 and the base 52 are sized for implantation into a dilated corpora cavernosum of the penis. The pushrod 28 is sized to be inserted through the base 52 and the bladder 50 and is employed to deliver the inflatable bladder 50 fully into the dilated distal portion of the corpora cavernosum. After implantation of the inflatable bladder 50, the plug 56 is inserted into a hole formed in the base 52 to create a pressurized seal for the penile prosthetic assembly 26, and then the base 52 is placed proximally in the dilated crus penis. A pressurized seal is a seal that can withstand pressures in a range from 10 pounds-per-square-inch (PSI) to 40 PSI (68.95 kPa to 275.8 kPa), preferably the pressurized seal withstands a pressure in a range from 15-35 PSI (103.43 kPa-241.33 kPa), and more preferably, the pressurized seal withstands a pressure above 15 PSI, for example in a range from 20-30 PSI (137.90 kPa-206.85 kPa).

The pushrod 28 is sized to have a length that is greater than the combined length of the inflatable bladder 50 and the base 52, which provides the advantage of full-length insertion of the inflatable bladder 50 into the distal penis without the use of a Keith needle or a tow suture. The pushrod 28 includes uniform markings 58 that allow the pushrod 28 to be used as a ruler. In one embodiment, the uniform markings 58 are segmented in 1 cm increments to advantageously allow measuring a depth of the corpora cavernosum in both the distal direction and the proximal direction. In one embodiment, the pushrod 28 is a rigid rod that is stiff and so configured to not flex or bend an appreciable manner in a lateral direction when pushing on the penile prosthetic assembly 26. One suitable example of a rigid rod is a stainless-steel pushrod 28.

Figure 2:
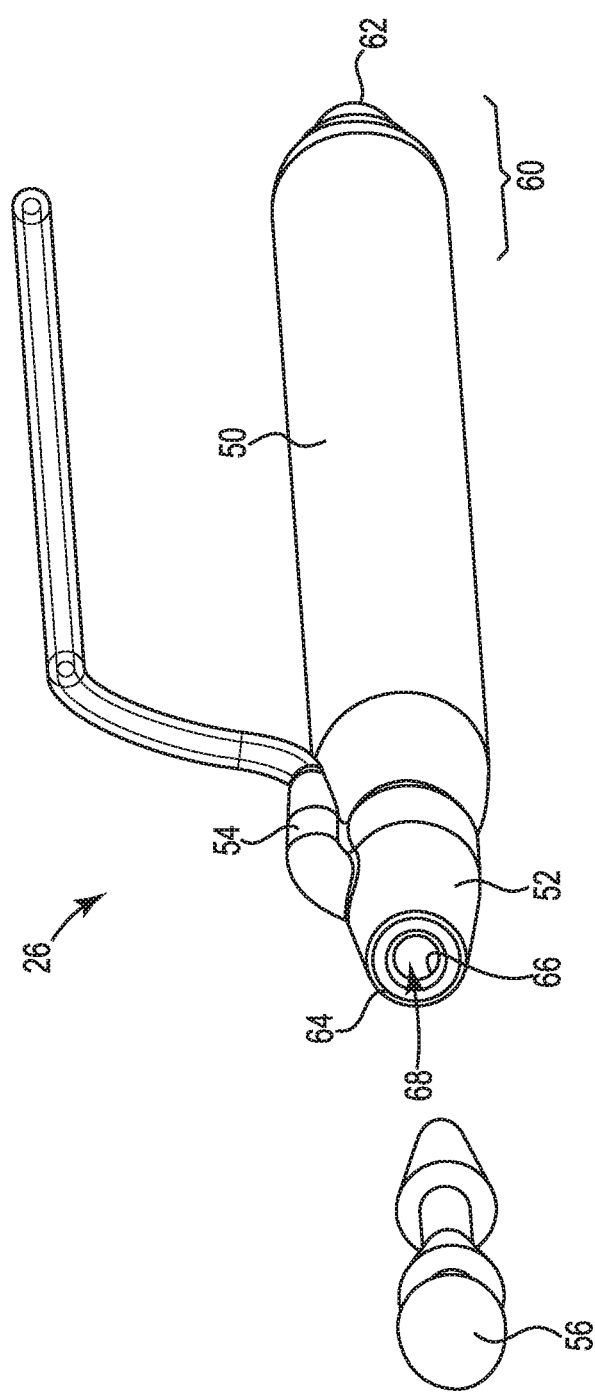
FIG. 2 is a perspective view of one of the penile prosthetic assemblies illustrated in FIG. 1.

FIG. 2 is a perspective view of one of the penile implants of the penile prosthetic assembly 26. The inflatable bladder 50 has a distal end portion 60 that terminates in a distal end 62. The base 52 is permanently bonded to the inflatable bladder 50. The base 52 has a proximal end 64 and a hole 66 is formed in the proximal end 64 to communicate with a channel 68 that extends longitudinally through an entire length of the base 52. The hole 66 and the channel 68 communicate with an interior of the inflatable bladder 50, where the hole 66 advantageously provides access into the penile prosthetic assembly 26 for implantation into the corpora cavernosum. The plug 56 is sized for insertion into the hole 66 after the inflatable bladder 50 has been placed inside of the distal corpora cavernosum. The tubing port 54 allows the penile prosthetic assembly 26 to be coupled with the pump 22 and the reservoir 24 shown in FIG. 1. As assembled, the plug 56 forms a proximal end of the penile prosthetic assembly 26.

Figure 3:
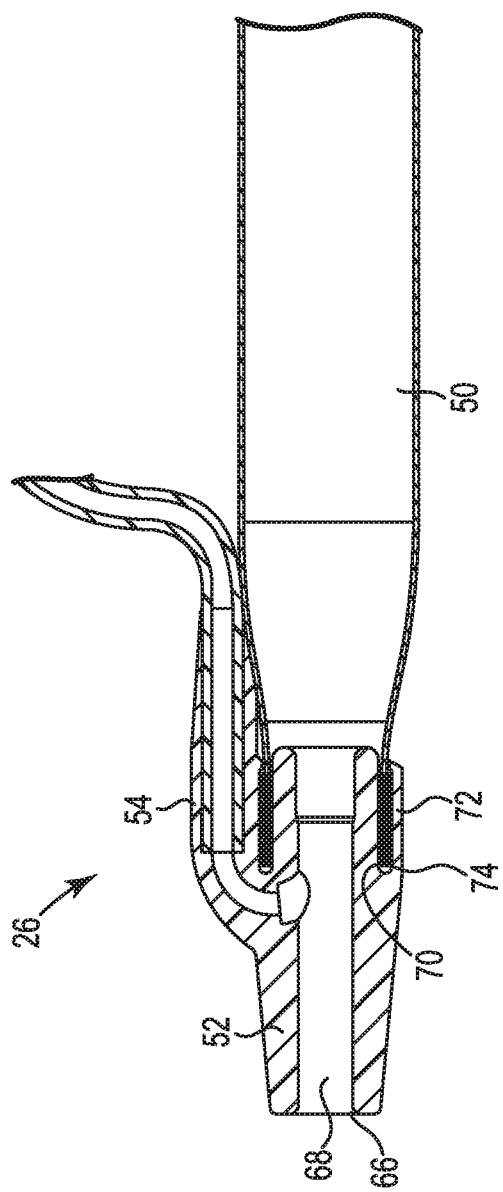
FIG. 3 is a cross-sectional view of the penile prosthetic assembly illustrated in FIG. 2.

FIG. 3 is a cross-sectional view of the proximal end portion of one of the penile implants of the penile prosthetic assembly 26. The channel 68 extends through an entire length of the base 52 to form an open communication between the hole 66 and the interior of the inflatable bladder 50.

In one embodiment, the base includes an annular recess 70 that forms a skirt 72 along an exterior surface of the base 52. The annular recess 70 is sized to receive a proximal end portion 74 of the inflatable bladder 50. In one embodiment, the proximal end portion 74 of the inflatable bladder 50 is permanently bonded within the annular recess 70 with an adhesive.

The tubing port 54 is in fluid communication with the channel 68, which is in fluid communication with an interior of the inflatable bladder 50.

Figure 4:
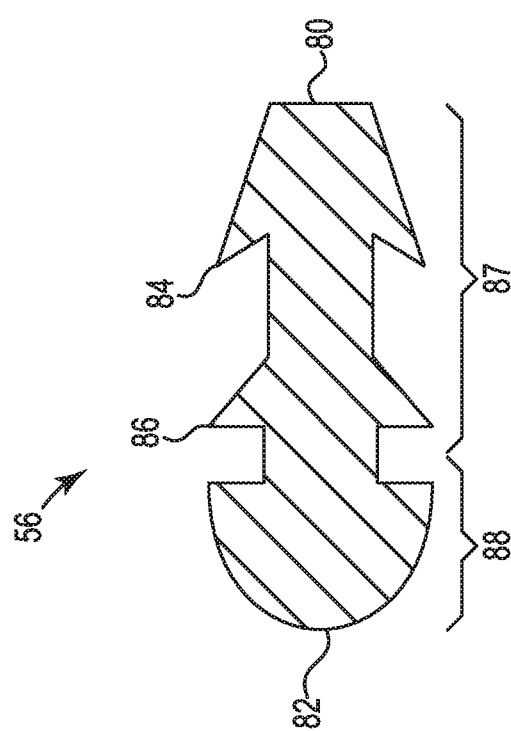
FIG. 4 is a cross-sectional view of one embodiment of a plug.

FIG. 4 is a cross-sectional view of one embodiment of the plug 56. The plug 56 extends from a distal end 80 to a proximal end 82 and includes at least one barb 84. In one embodiment, the plug 56 includes a first barb 84 and a second barb 86. The barbs 84, 86 are configured to engage with the channel 68 (FIG. 2) and provide a pressurized seal for the penile prosthetic assembly 26 (FIG. 2). The number of barbs distributed along a length of the plug may suitably range from one barb to several barbs, and thus the depth of engagement between the barbs 84, 86 and the channel 68 in the base 52 may also vary. Although two barbs are illustrated, embodiments with three or more barbs have been contemplated and deemed useful. The barb 84 has an angle of engagement relative to the stem of the plug 56 of about 60 degrees measured on the proximal side of the barb, and the barb 86 has an angle of engagement relative to the stem of the plug 56 of about 90 degrees measured on the proximal side of the barb. Thus, the angle of each barb relative to the stem of the plug 56 may vary. Alternatively, a plurality of barbs is provided and each barb has an equal angle of engagement relative to the stem of the plug 56, and that angle could be an acute angle of less than 90 degrees, or 90 degrees as for barb 86, or an obtuse angle of greater than 90 degrees.

In one embodiment, the plug 56 is formed as a single integrated piece from a single polymer. For example, suitable plugs 56 include a plug formed homogeneously from one of the following polymers: polypropylene, polyethylene, nylon, polyurethane, silicone, or a block styrene.

In one embodiment, the plug 56 is formed from a polymer system with a barb section 87 that forms the barbs 84, 86 being fabricated from a polymer having a first durometer and a proximal section 88 including the proximal end 82 being fabricated from a polymer having a second durometer, where the second durometer is of a lower value than the first durometer. In other words, embodiments provide for the proximal end 82 and the proximal section 88 of the plug 56 to be softer than the distal end 80 and the barb section 87 of the plug 56. The softer proximal section 88 contributes to patient comfort since this portion of the plug 56 is in contact with tissue when the prosthetic is implanted.

In one embodiment, the plug 56 is radiopaque, which is useful when viewing the status of the implant with an x-ray machine. Some implants are explanted, and a radiopaque plug 56 allows the surgeon to ensure a complete removal of the implant.

Figure 5:
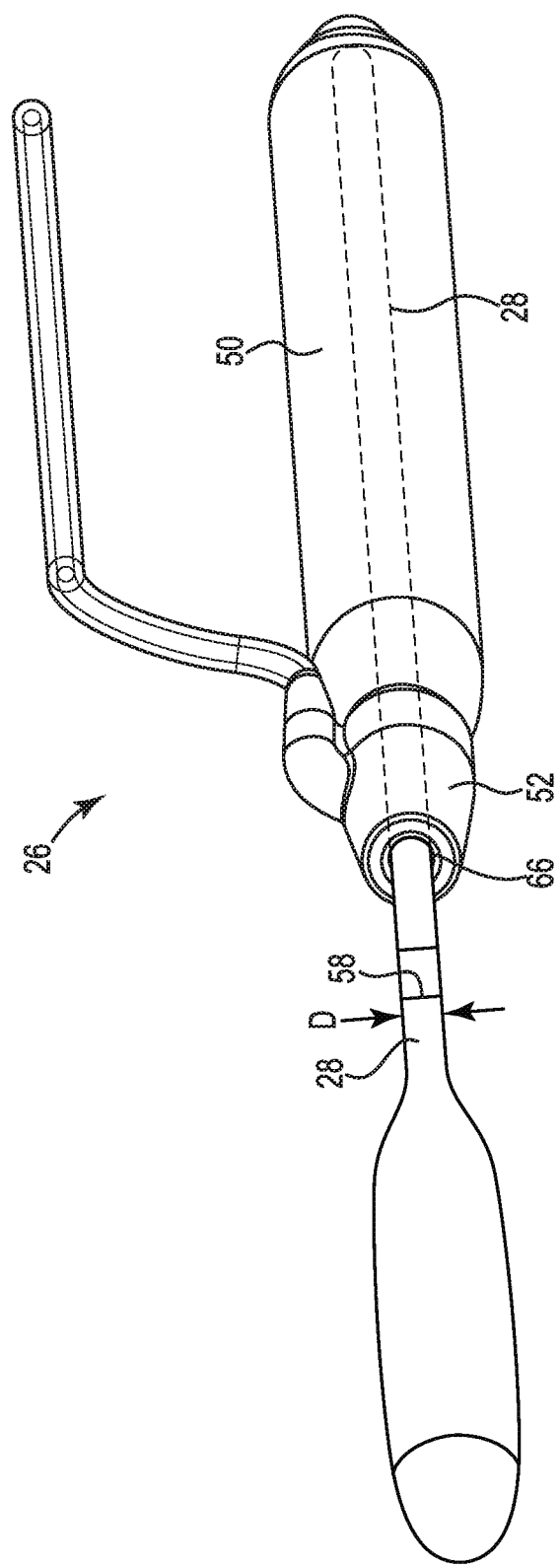
FIG. 5 is a perspective view of one embodiment of a pushrod inserted through a base and an inflatable bladder of the penile prosthetic assembly illustrated in FIG. 2.

FIG. 5 is a perspective view of the pushrod 28 inserted into the hole 66 to provide for placement of the inflatable bladder 50 into a dilated corpora cavernosum of the penis. In one embodiment, a diameter D of the pushrod 28 is selected to be smaller than the diameter of the hole 66 such that the pushrod has a clearance fit relative to the hole 66. A clearance fit is a description of the relative diameters between the pushrod 28 and the hole 66 that allows the pushrod 28 to slide into the hole 66 with no interference from the channel 68. A clearance fit is contrasted to a slip fit, where a slip fit is a description of relative diameters in which the pushrod would slide with a measurable level of interference (friction) relative to the hole 66.

Figure 6:
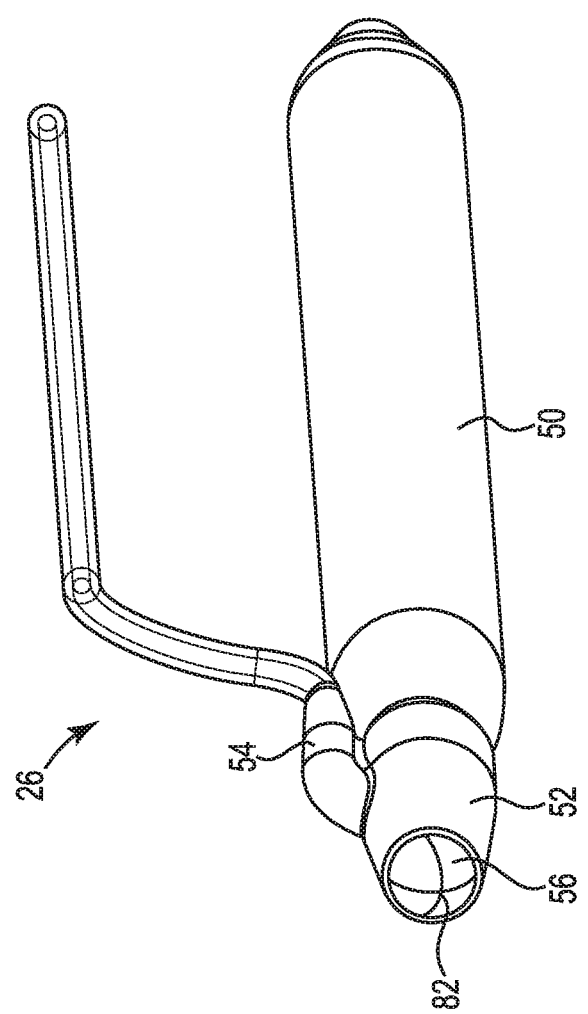
FIG. 6 is a perspective view of the plug illustrated in FIG. 4 inserted into the penile prosthetic assembly illustrated in FIG. 2.

FIG. 6 is a perspective view of one of the penile implants of the penile prosthetic assembly 26 with the plug 56 secured into the hole 66 formed in the base 52.

The following is a description of one suitable implantation procedure with reference to FIG. 5 and FIG. 6.

The penis of the patient is incised in a corporotomy to expose a pair of corpora cavernosa that are aligned axially in a side-by-side orientation within the penis. A cutting implement, such as a curved Mayo scissors, is employed to penetrate the fascia of the penis and form an opening accessing each corpora cavernosum. Subsequently, each corpora cavernosum is dilated (opened) with an appropriate dilation tool to form a recess that is sized to receive one of the two cylinders of the penile prosthetic.

The pushrod 28 is inserted into each of the pair of the dilated corpora cavernosum to measure a distal length of the corpora cavernosum within the external penis. Subsequently, the pushrod 28 is inserted into the crus penis to measure a proximal length of the dilated crus penis. The addition of the distal length and the proximal length provides an estimate of a suitable total length for the selection of the penile implant.

The penile prosthetic assembly 26 of the selected length is implanted into the dilated corpora cavernosum by inserting the pushrod 28 into the hole 66, through the channel 68, and through a length of the inflatable bladder 50. The inflatable bladder 50 is pushed to a distal end of the dilated corpora cavernosum. The pushrod 28 is removed from the penile prosthetic assembly 26 since the pushrod 28 is provided with a clearance fit relative to the hole 66.

The plug 56 is inserted into the hole 66 to provide a pressurized seal. The base 52 of the penile prosthetic assembly 26 is inserted into the dilated crus penis. The tubing port 54 is coupled to the tubing 36 of the pump 22 (FIG. 1) using the connector 38. After the surgeon has suitably connected the tubing of the penile prosthetic assembly 26 to the pump 22 and the reservoir 24, liquid will be introduced into the inflatable bladder 50 to ensure appropriate inflation of the inflatable bladder 50 without leakage. Thereafter, the surgeon ensures that the connections have been suitably made and subsequently implants the reservoir 24 into a space within the abdomen and implants the pump 22 within a space within the scrotum.

Figure 7:
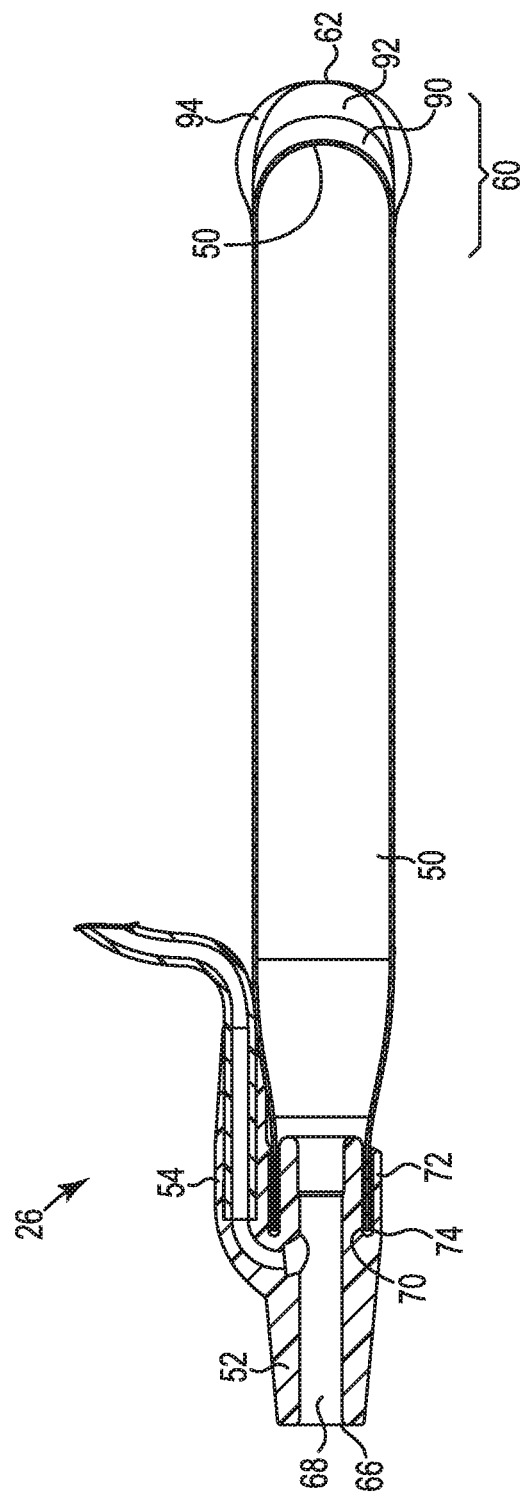
FIG. 7 is a cross-sectional view of one embodiment of a distal end portion of the inflatable bladder of the penile prosthetic assembly illustrated in FIG. 2.

FIG. 7 is a cross-sectional view of one embodiment of one of the two penile implants of the penile prosthetic assembly 26. Advantages of the embodiments described above obviates the use of a Keith needle during implantation of a penile prosthetic. Consequently, instead of having a hole formed in a distal end portion of the prosthetic to accommodate a suture, the distal end portion 60 may be fabricated to include a more bulbous or a more comfortable tip. In one embodiment, the inflatable bladder 50 forms an interior surface of the prosthetic, and one or more distal end layers can be added to give the prosthetic an improved feel for the user. A first layer 90 is coupled to the inflatable bladder 50, a second layer 92 is provided to give the prosthetic an increase in length, and a third layer 94 is provided to give the prosthetic an increase in girth. In one embodiment, the second layer 92 provides a soft, tissue-like layer and the third layer 94 provides an artificial glans penis. The layers 90, 92, and 94 combine to provide an artificial glans penis on the penile prosthetic assembly 26 characterized by a bulb-shape at the distal end portion that has a width that is wider than a width of the inflatable bladder 50. The layers 90, 92, and 94 included bonded-on silicone as one exemplary embodiment.

Figure 8:
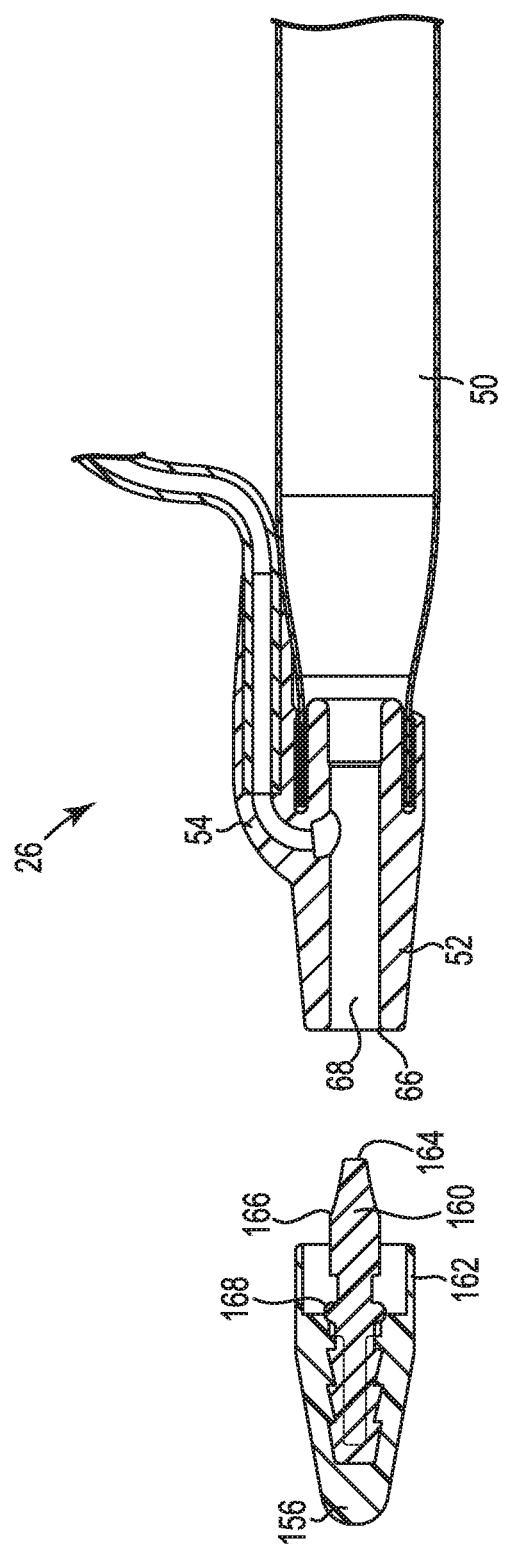
FIG. 8 is a cross-sectional view of one embodiment of a plug that is adapted to be inserted into the penile prosthetic assembly illustrated in FIG. 2.
Figure 9:
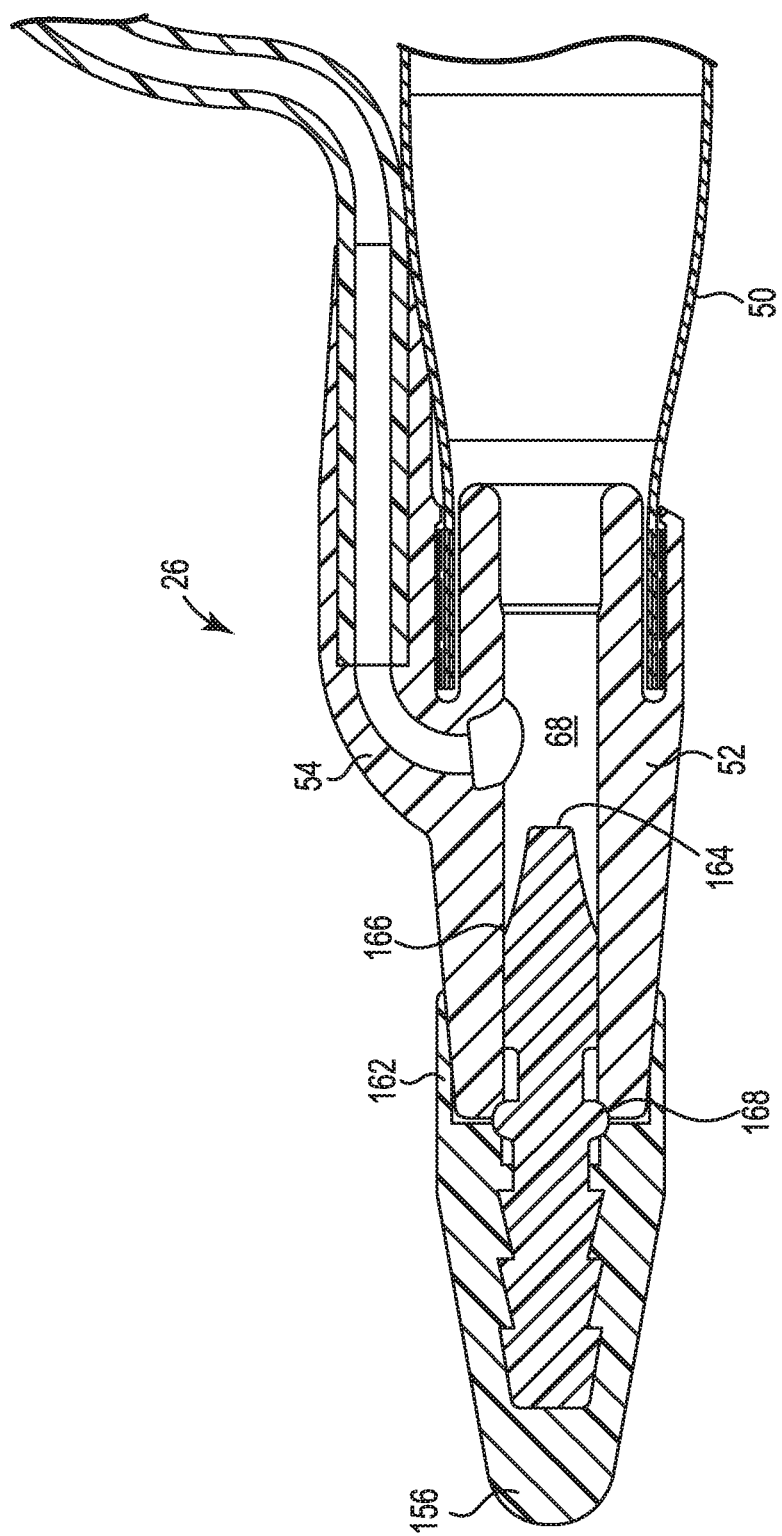
FIG. 9 is a cross-sectional view of the plug illustrated in FIG. 8 inserted into the penile prosthetic assembly.

FIG. 8 is a cross-sectional view of the inflatable bladder 50 and the base 52 of the penile prosthetic 26 provided with one embodiment of a plug 156. FIG. 9 is a cross-sectional view illustrating the plug 156 inserted into the base 52.

The plug 156 provides a combination seal and rear tip extender adapted to increase a length of the penile prosthetic 26. In one embodiment, the plug 156 includes a projection 160 that is sized to be inserted into the channel 68 to provide a pressurized seal, and an annular skirt 162 that is sized to couple to the exterior surface of the base 52. In one embodiment, the projection 160 extends in a distal direction out from and away from the annular skirt 162. The projection 160 includes a distal end 164, a sealing surface 166 adapted to seal inside of the channel 68, and a sealing surface 168 adapted to seal relative to the hole 66.

The plug 156 provides a rear tip extender adapted to increase a length of the penile prosthetic 26. A rear tip extender is useful to allow a surgeon to adjust a length of the implant based upon a depth of a dilated crus penis. Some crus penis sections become fibrotic and are difficult to dilate. Providing the plug 156 as both a pressurized seal feature and a rear tip extender allows the surgeon to customize each penile implant based upon a resulting crus penis dilation. It is advantageous to have a set of rear tip extenders of varying lengths. In one embodiment, a set of five plugs 156 is provided, where the setoff five plugs 156 have lengths of, for example, 2 cm, 3 cm, 4 cm, 5 cm, and 6 cm.

Figure 10:
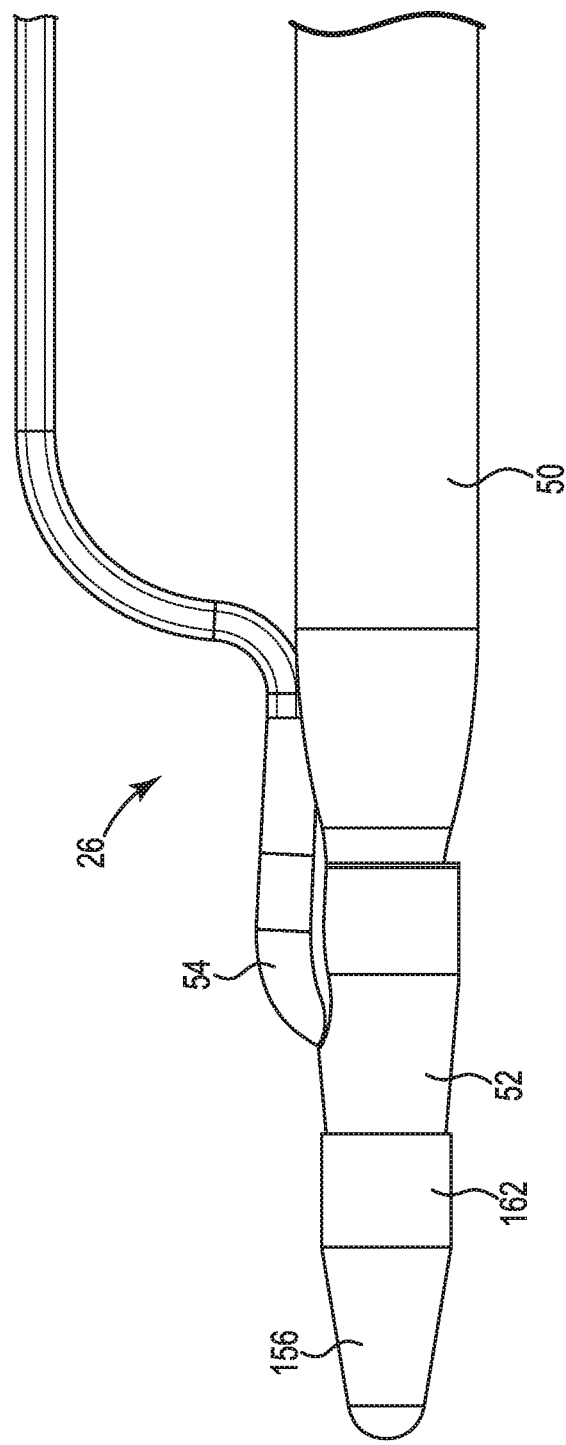
FIG. 10 is a side view of the plug illustrated in FIG. 8 inserted into the penile prosthetic assembly.

FIG. 10 illustrates the plug 156 inserted into the base 52 with the annular skirt 162 coupled in a streamlined fashion to the base 52. The plug 156 increases a length of the penile prosthetic 26. A variety of plugs 156 may be provided, where each plug 156 has an incrementally different length. In this manner, the surgeon is provided with options to select a plug 156 having a length that is suited for a measured depth of the crus penis. For example, a set of plugs may be provided in a kit in 2 centimeter increments, so that the kit includes a 2 cm plug, a 4 cm plug, a 6 cm plug, etc.

Figure 11:
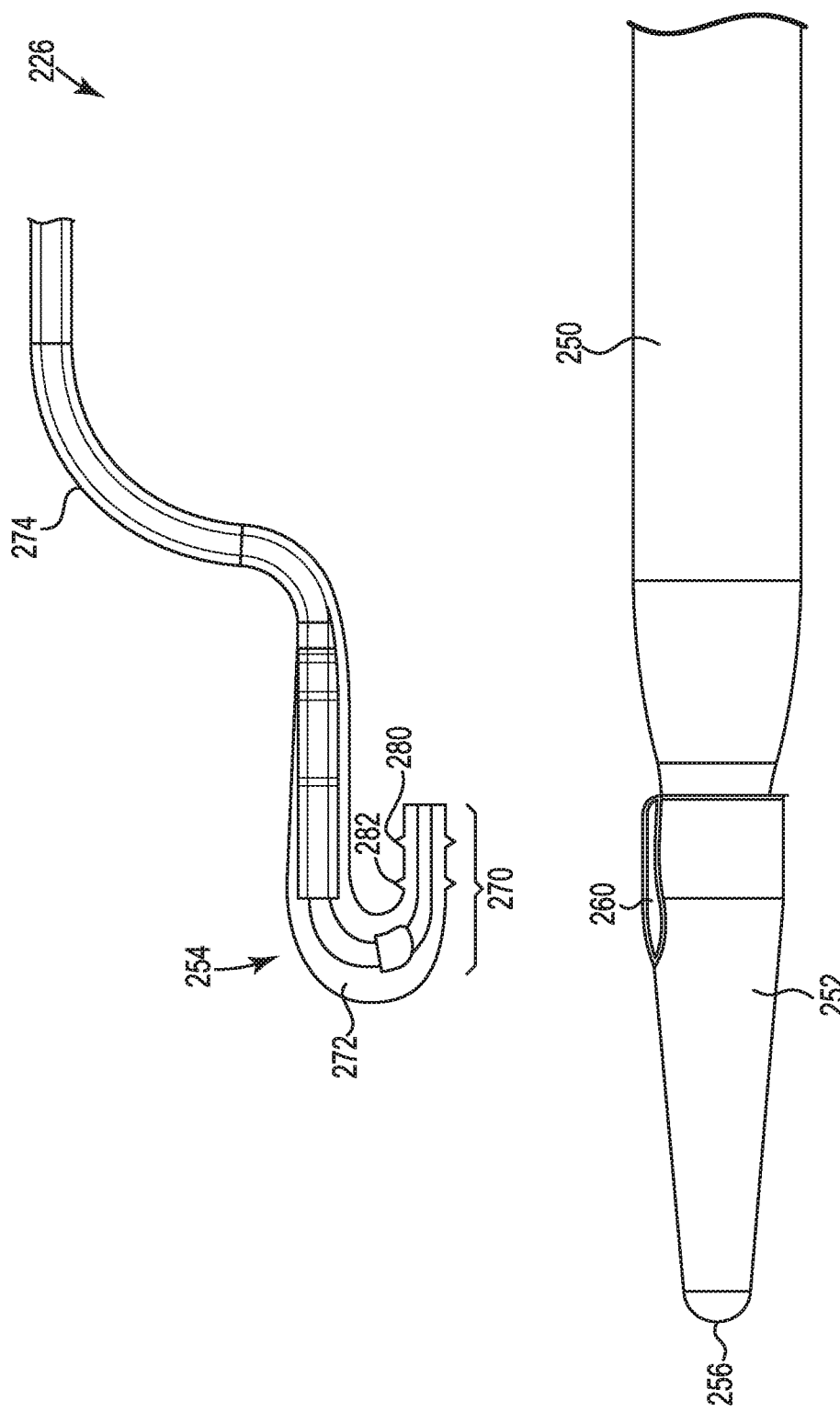
FIG. 11 is a perspective view of one embodiment of a penile prosthetic assembly including a tubing port portion insertable into a penile prosthetic assembly.

FIG. 11 is a perspective view of one embodiment of one penile implant of a penile prosthetic 226 including an inflatable bladder 250, a base 252 connected to the inflatable bladder 250, and a tubing assembly 254 having a portion that is insertable into the base 252 to provide the penile prosthetic 226 with a pressurized seal.

The inflatable bladder 250 extends to a rounded distal end that is adapted to be inserted into a glans penis. The base 252 gradually tapers to a rounded proximal end 256 that is adapted to be inserted into a crus penis.

In one embodiment, the base 252 includes an opening 260 that provides access to the interior surface of the inflatable bladder 250. The opening 260 allows the surgeon to use a tool to access and subsequently push the inflatable bladder 250 into a dilated corpora cavernosum.

In one embodiment, the tubing assembly 254 includes a seal portion 270, a neck portion 272, and tubing 274. The seal portion 270 includes engagement barbs 280, 282 that are adapted to engage with a channel formed inside of the opening 260 of the base 252. The neck portion 272 is adapted to couple with the opening 260 to secure the tubing assembly 254 to the exterior portion of the base 252. The tubing 274 is attachable to the pump 22 illustrated in FIG. 1.

Figure 12:
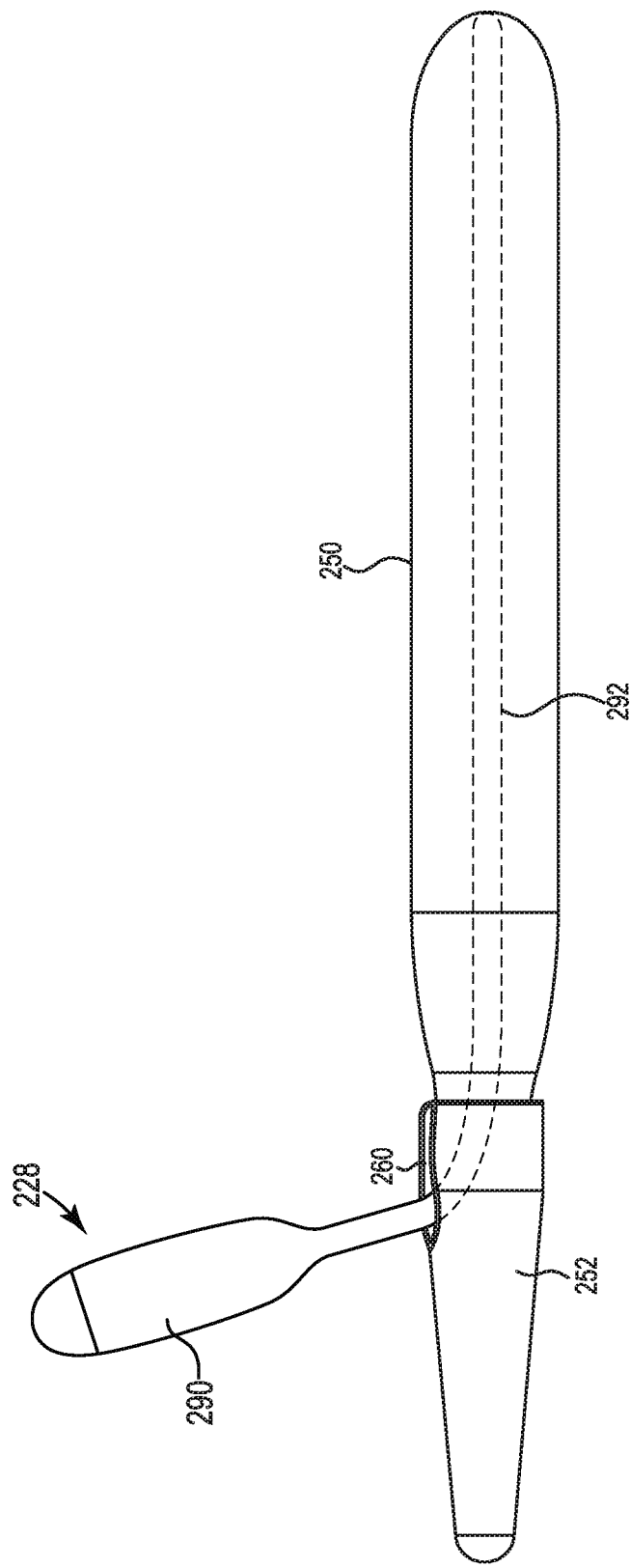
FIG. 12 is a side view of a flexible insertion aid inserted into the penile prosthetic assembly illustrated in FIG. 11.

FIG. 12 is a side view of an insertion aid 228 inserted into the opening 260 and useful for pushing the inflatable bladder 250 distally into a dilated corpora cavernosum.

In one embodiment, the insertion aid 228 is a pushrod 228 that includes a handle 290 and a flexible rod 292. The flexible rod 292 is adapted to be bent at an angle up to 180 degrees, which allows the flexible rod 292 to be inserted through the opening 260 and bent at an angle of approximately 90 degrees for traversing into the inflatable bladder 250. In one embodiment, the flexible rod 292 is formed from a flexible polymer such as polyurethane or silicone. The pushrod 228 is removed from the opening 260 after the pushrod 228 has appropriately positioned the inflatable bladder 250 into the corpora cavernosum.

In one embodiment, the insertion aid 228 is an inflatable balloon 228 that is intra-operatively insertable into the inflatable bladder 250 of the penile prosthetic 226. In one embodiment, the insertion aid 228 is an inflatable balloon 228 that is pre-operatively placed in the inflatable bladder 250 of the penile prosthetic 226 during manufacturing. It has been discovered that the distal portion of the inflatable bladder 250 can tend to slip in a proximal direction after the inflatable bladder 250 has been inserted into the distal corpora cavernosum and the pushrod 228 (above) has been removed. This slippage is counter to the goal of placing the distal end portion of the inflatable bladder 250 into the distal corpora. Thus, one embodiment includes providing the insertion aid 228 as an inflatable balloon 228 inside of the bladder 250. The insertion aid 228 is inflated with water or saline to provide the bladder 250 with column strength, which is useful in both placing the bladder 250 distally and in holding the bladder 250 inside of the corpora after placement. The proximal end of the base 252 is inserted into the dilated proximal crus penis with the inflated balloon of the insertion aid 228 maintaining the bladder 250 in the distal corpora, which overcomes any tendency of the inflatable bladder 250 to slip in the proximal direction. After both the distal portion of the bladder 250 and the proximal portion of the base 252 have been implanted in the dilated penis, the balloon 228 is deflated and the insertion aid 228 is withdrawn from the bladder 250.

Figure 13:
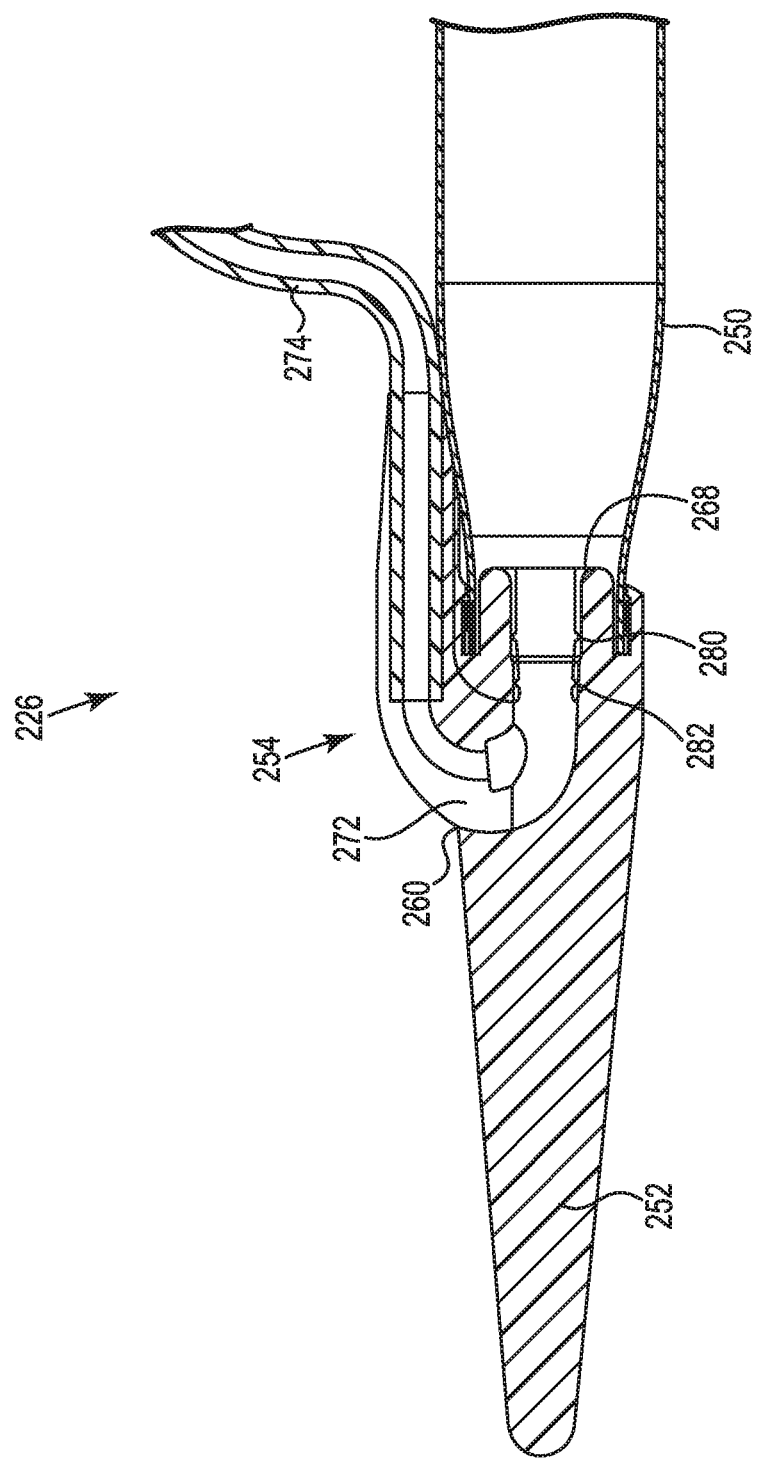
FIG. 13 is a cross-sectional view of the tubing port illustrated in FIG. 11 coupled to the penile prosthetic assembly illustrated in FIG. 11.
Figure 14:
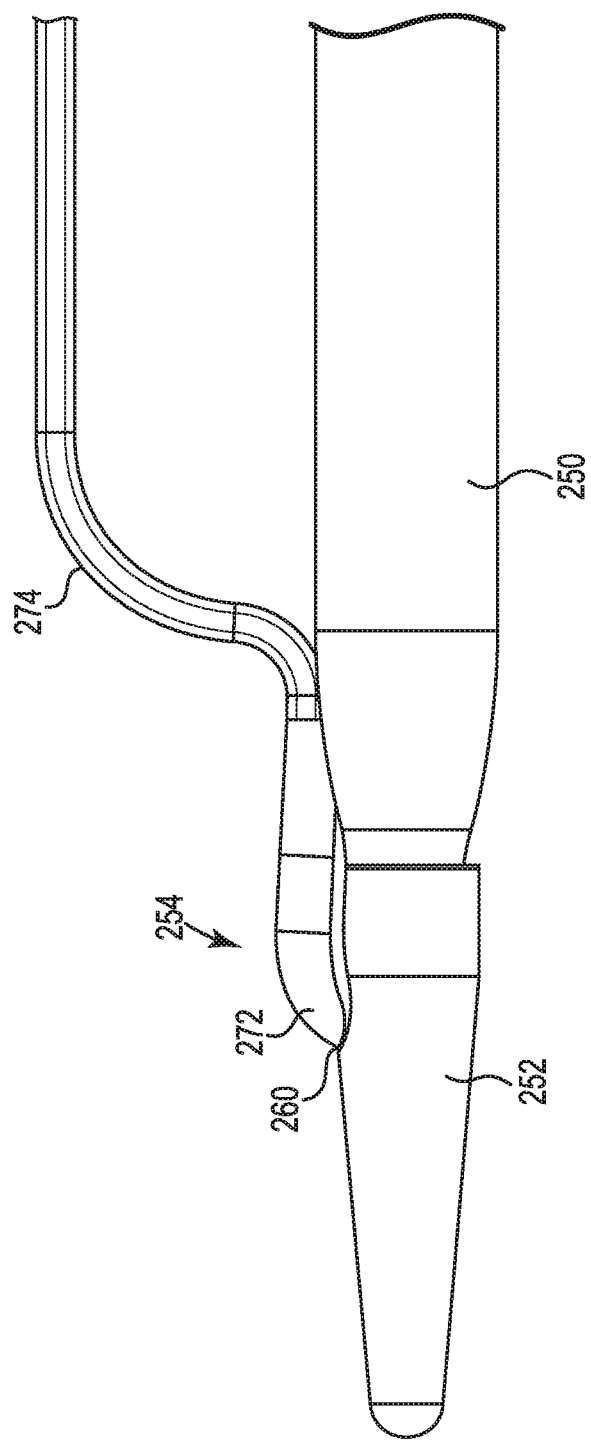
FIG. 14 is a perspective view of the assembled tubing port and a portion of the penile prosthetic assembly as illustrated in FIG. 13.

FIG. 13 is a cross-sectional view and FIG. 14 a is a side view of the tubing assembly 254 inserted into the base 252. The first barb 280 and the second barb 282 are engaged within a channel 268 formed inside of the base 252. The neck 272 is sealed within the opening 260.

The following is a description of one suitable implantation procedure with reference to FIGS. 11-14.

The penis of the patient is incised in a corporotomy to expose a pair of corpora cavernosa that are aligned axially in a side-by-side orientation within the penis. A cutting implement, such as a curved Mayo scissors, is employed to penetrate the fascia of the penis and form an opening accessing each corpora cavernosum. Subsequently, each corpora cavernosum is dilated (opened) with an appropriate dilation tool to form a recess that is sized to receive one of the two cylinders of the penile prosthetic.

A penile prosthetic assembly 226 of the selected length is implanted into the dilated corpora cavernosum by inserting the pushrod 228 (FIG. 12) into the hole 260, through the channel 268 (FIG. 13), and through a length of the inflatable bladder 250 (FIG. 12). The inflatable bladder 250 is pushed to a distal end of the dilated corpora cavernosum. The pushrod 228 is removed from the penile prosthetic assembly 226 since the pushrod 228 is provided with a clearance fit relative to the hole 260.

The tubing assembly 254 is inserted into the hole 260 and the barbs 280, 282 engage with the channel 268 formed in the base 252 (FIG. 13). Coupling of the tubing assembly 254 to the base 252 provides both a pressurized seal and a conduit to the pump/reservoir. For example, the tubing 274 (FIG. 11) is coupled to the tubing 36 of the pump 22 (FIG. 1) using the connector 38.

After the surgeon has suitably connected the tubing 274 to the pump 22 and the reservoir 24, liquid will be introduced into the inflatable bladder 250 to ensure appropriate inflation of the inflatable bladder 50 without leakage. Thereafter, the surgeon ensures that the connections have been suitably made and subsequently implants the reservoir 24 into a space within the abdomen and implants the pump 22 within a space within the scrotum.

Although specific embodiments have been illustrated and described, it will be appreciated by those of ordinary skill in the art that a variety of alternate and equivalent implementations may be substituted for the specific embodiments shown and described without departing from the scope of the present invention. This application is intended to cover any adaptations or variations of the kind of medical devices described above. Therefore, it is intended that this invention be limited only by the claims and their equivalents.

What is claimed is:

1. An inflatable penile prosthetic system, the system comprising:
   a pump adapted move liquid out of a reservoir, with the pump attachable to the reservoir with a first section of tubing;
   a penile prosthesis including a base connected to an inflatable bladder, where the inflatable bladder has a bladder wall that that forms an interior surface of the inflatable bladder and a distal end sized for placement within a glans penis, and the base has a side wall extending between a distal end connected to the inflatable bladder and a proximal end, where the base includes an opening formed in the side wall of the base communicating with an interior channel formed in the base, and the opening and the interior channel are in fluid communication with the interior surface of the inflatable bladder; and
   a tubing assembly insertable into the opening formed in the side wall of the base;
   wherein the tubing assembly includes a neck portion extending between a seal portion that is adapted to seal within the opening formed in the base and a tubing portion that is adapted to couple with the pump.

2. The system of claim 1, wherein the seal portion of the tubing assembly includes at least one barb that is adapted to engage with the interior channel formed in the base.

3. The system of claim 1, wherein the seal portion of the tubing assembly includes a first barb and a second barb, where the first barb and the second barb are configured to engage with the interior channel formed in the base to provide a pressurized seal for the penile prosthetic system.

4. The system of claim 1, wherein the neck portion and the seal portion of the tubing assembly form a C-shape.

5. The system of claim 1, wherein the side wall of the base tapers between the distal end and the proximal end of the base.

6. The system of claim 1, wherein the side wall of the base tapers from the distal end to converge to the proximal end of the base.

7. The system of claim 1, wherein the opening is adapted to allow a tool to access the inflatable bladder through the side wall of the base.

8. A kit of parts, the kit comprising:
   a pump adapted move liquid out of a reservoir, with the pump attachable to the reservoir with a first section of tubing;
   a penile prosthesis including a base connected to an inflatable bladder, where the inflatable bladder has a bladder wall that that forms an interior surface of the inflatable bladder and a distal end sized for placement within a glans penis, and the base has a side wall extending between a distal end connected to the inflatable bladder and a proximal end, where the base includes an opening formed in the side wall of the base communicating with an interior channel formed in the base, and the opening and the interior channel are in fluid communication with the interior surface of the inflatable bladder;
   a tubing assembly insertable into the opening formed in the side wall of the base;
wherein the tubing assembly includes a neck portion extending between a seal portion that is adapted to seal within the opening formed in the base and a tubing portion that is adapted to couple with the pump;
   a push rod having a diameter that is sized for insertion into the opening; and
   a plurality of connectors including a first connector provided to attach the first section of tubing to reservoir tubing and a second connector provided to attach the tubing portion to tubing of the pump.

9. The kit of parts of claim 8, wherein the push rod has a length that is adapted to extend from the distal end of the inflatable bladder, through the interior channel formed in the base, and out of the opening formed in the side wall of the base.

10. The kit of parts of claim 8, wherein the pushrod includes uniform markings that allow the pushrod to be used as a ruler.

* * * * *